United States Patent
Morgan et al.

(10) Patent No.: US 6,489,167 B1
(45) Date of Patent: *Dec. 3, 2002

(54) RETROVIRAL PACKAGING CASSETTES AMPLIFIED IN THE CYTOPLASM BY AUTOCATALYTIC TOGAVIRUS VECTORS

(75) Inventors: Richard Morgan, Columbia, MD (US); Jarmo Wahlfors, Columbia, MD (US); Kleanthis Xanthopoulos, La Jolla, CA (US)

(73) Assignee: The Government of the United States as represented by the Secretary of the Department of Human Services, Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/147,920
(22) PCT Filed: Sep. 24, 1997
(86) PCT No.: PCT/US97/17049
§ 371 (c)(1), (2), (4) Date: Jul. 12, 1999
(87) PCT Pub. No.: WO98/13511
PCT Pub. Date: Apr. 2, 1998

Related U.S. Application Data
(60) Provisional application No. 60/026,666, filed on Sep. 25, 1996.

(51) Int. Cl.[7] .............................................. C12N 15/86
(52) U.S. Cl. .................... 435/456; 435/457; 435/320.1; 424/218.1
(58) Field of Search ................................. 435/69.1, 440, 435/320.1, 218.1; 424/199.1

(56) References Cited

FOREIGN PATENT DOCUMENTS

| WO | WO 92/10578 | 6/1992 | ........... C12N/15/86 |
|---|---|---|---|
| WO | WO 95/10578 | 9/1995 | ........... C12N/15/86 |

OTHER PUBLICATIONS

Li and Garoff, Production of Infectious recombinant Moloney murine leukemia virus particles in BHK cells using Semliki Forest virus–derived RNA expression vectors, *Proc. Nat'l Acad. Sci*, 99:11656–11663 (10/96).

Markowitz et al., A Safe Packaging Line for Gene Transfer: Separating Viral Genes on Two Different Plasmids, *Journal of Virology*, 62(4):1120–1124, (4/88).

Roman et al., Circulating Human or Canine Factor IX from Retrovirally Transduced Primary Myoblasts and Established Myoblast Cell Lines Grafted into Murine Skeletal Muscle, *Somatic Cell and Molecular Genetics*, 18(3):247–258 (1992).

*Primary Examiner*—Laurie Scheiner
*Assistant Examiner*—Jeffrey S. Parkin
(74) *Attorney, Agent, or Firm*—Townsend and Townsend and Crew LLP

(57) ABSTRACT

This invention provides a Togavirus-amplified retrovirus vector and a novel method for packaging a retrovirus cassette that contains a heterologous nucleic acid, which is amplified in a packaging cell cytoplasm by a Togavirus vector. The retroviral cassette is packaged into infectious retrovirus particles by retroviral packaging cells. These retroviral particles carrying the retroviral packaging cassette are then used to infect host cells.

13 Claims, 4 Drawing Sheets

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 91 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

```
GGCCGCGGAT CCGCGCCAGT CTTCCGATAG ACTGCGTCGC CCGGGTACCC GTGTATCCAA      60

TAAACCCTCT TGCAGTTGCA GGATCCAAGC T                                    91
```

(2) INFORMATION FOR SEQ ID NO:2:

(i) SEQUENCE CHARACTERISTICS:
      (A) LENGTH: 109 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

```
GAGCTCAATA AAAGAGCCCA CAACCCCTCA CTCGGGATTG GTGCGTTAAT ACACAGAATT      60
```

-continued

```
CTGATTGGAT CCGCGCCAGT CCTCCGATTG ACTGAGTCGC CCGGGTACC                    109

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

GGGCCCATTT AAATCCTAGG                                                     20

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

ATTGGTGCGT TAATACACAG AATTCTGATT GGATCC                                   36

(2) INFORMATION FOR SEQ ID NO:5:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

ACCTCTACGG CGGTCCTAGA TTGGTGCGTT AATACACAGA ATTCTGATTG GATCCCGGG          59
```

RETROVIRAL PACKAGING CASSETTES AMPLIFIED IN THE CYTOPLASM BY AUTOCATALYTIC TOGAVIRUS VECTORS

CROSS REFERENCE TO RELATED APPLICATIONS

This application claims the benefit of the filing date of U.S. Ser. No. 60/026,666, filed Sep. 25, 1996.

FEDERALLY SPONSORED RESEARCH OR DEVELOPMENT

Not applicable.

FIELD OF THE INVENTION

This invention provides a Togavirus-amplified retrovirus vector and a novel method for packaging a retroviral cassette that contains a heterologous nucleic acid, which is self-amplified in a packaging cell cytoplasm.

BACKGROUND OF THE INVENTION

Retrovirus vectors are currently the most advanced system available for mammalian gene therapy. These vectors are preferred for gene therapy because of their unique life cycle, which is divided into two phases: RNA and DNA. Wild-type retroviruses infect cells with a single-stranded RNA genome. This viral RNA genome is reverse-transcribed into a double-stranded DNA provirus, which integrates into the host genome. The viral RNA genome is then transcribed in the nucleus from the provirus. For the most part, the provirus functions as a cellular gene after integration into the genome. This characteristic is desirable for gene therapy as it provides a relatively stable copy of the gene of interest in the host genome. This characteristic, however, also creates a drawback for the production of recombinant vectors used in gene therapy: The nuclear-based transcription of the RNA genome limits the sequences that can be included in a recombinant retrovirus vector, due to nuclear RNA processing of the viral genome prior to packaging. Thus, the nuclear-based RNA synthesis of the retroviral genome results in the removal of intron sequences and other flanking and regulatory sequences from the retroviral RNA.

Typically, recombinant retrovirus vectors are constructed as a DNA provirus having a heterologous expression cassette. These vectors, in the form of recombinant DNA plasmids, are transduced into packaging cells. The DNA vector is transcribed in the nucleus, and the resulting RNA genome is processed in the nucleus before moving to the cytoplasm for packaging. Thus, heterologous genes included in the vector are processed before they are packaged into virus particles for gene therapy. The heterologous genes in retrovirus vectors, therefore, do not usually include complex, more gene-like features such as introns, polyadenylation signals, and flanking sequences because of this drawback in the vector system. Furthermore, the production of full-length retrovirus RNA can be severely impaired by transcriptional polyadenylation signals and transcriptional stop signals in 3' flanking regions. Finally, often cDNAs are not expressed well in the nucleus due to the absence of processing signals (Chuah et al., Hum. Gene Ther. 6: 1363–1377 (1995)).

Other strategies have been used to construct retrovirus vectors that contain complex heterologous genes, but these systems have been unsuccessful. Attempts to integrate gene-like constructs in reverse orientation have been difficult mostly due to instability of these constructs and low vector titers (Jonsson et al., Hum. Gene Ther. 6: 611–623 (1995); Cone et al., Science 236: 954–957 (1987); Cosset et al., J. Virol. 69: 7430–7436 (1995)). These intron and flanking sequences, however, are often essential for efficient, stable in vivo gene expression (see, e.g., Brinster et al., Proc. Natl. Acad. Sci. U.S.A. 85: 836–840 (1988); Palmiter et al., Proc. Natl. Acad. Sci. U.S.A. 87: 6024–6028 (1991)). This lack of complexity thus limits the use of retrovirus vectors for the expression of heterologous genes in gene therapy.

Alphaviruses are a genus of the Togavirus family that have a positive strand, single-stranded RNA genome. Unlike retroviruses, Alphaviruses carry out their intracellular activities, including replication, in the cytoplasm. Certain members of the Alphavirus family are well-characterized, in particular Semliki Forest virus (SFV) and Sindbis virus (Liljestrom & Garoff, Biotechnology 9: 1356–1361 (1991); Rice et al., J. Virol. 61: 3809–3819 (1987)). Semliki Forest virus (SFV)-based expression systems have been used to express heterologous genes. In the SFV system, viral replicase proteins are translated from the viral RNA genome. The replicase proteins recognize specific viral replicase promoters and amplify SFV RNA. Eukaryotic RNA polymerases and nuclear RNA processing machinery are not involved in the synthesis of SFV RNA. However, Alphaviruses do not provide an integrated copy of the heterologous gene of interest in the host genome. Therefore, there is a need for a vector that provides stable and efficient expression of heterologous genes.

SUMMARY OF THE INVENTION

The present invention provides Togavirus-amplified retrovirus vectors and a novel method of packaging heterologous nucleic acid sequences in a retroviral cassette using a Togavirus system. These heterologous nucleic acids can include, for example, full length genes, cDNAs, introns, flanking regions, polyadenylation signals, or other sequences that are normally incompatible with expression of the retrovirus RNA in the cell nucleus. This system liberates vector design from constraints imposed by nuclear RNA transcription. To achieve this result, nuclear transcription and processing of retrovirus RNA in the packaging cell must be avoided. By using Togavirus mediated RNA self-amplification in the cytoplasm, the present invention provides vectors and a method of bypassing the DNA provirus stage during packaging. This invention therefore permits the production of retrovirus vectors that contain complex heterologous genes or cDNAs. Thus, the vectors and method of the invention are useful for gene therapy. An additional advantage of the Togavirus-amplified retrovirus vector production system is that it is able to produce high titers of retrovirus particles, due to its self-amplification capabilities.

The method of the invention includes first, selecting a packaging cell that produces retroviral components, including reverse transcriptase, integrase, gag proteins, and envelope proteins. Second, the cell is transduced with RNA sequences. These RNA sequences encode: the replicase gene cluster of a Togavirus, which is operably linked to a ribosomal binding site recognized by ribosomes of the packaging cell; and a Togavirus replicase target sequence, which contains a replicase promoter operably linked to a replicase amplification region. The replicase amplification region consists of a subgenomic promoter and the retroviral packaging cassette. The cassette comprises R and U5 regions at the 5' end, reverse transcriptase recognition sites, a retroviral packaging sequence, a eukaryotic expression cassette that contains a promoter operably linked to a heterologous nucleic acid, and U3 and R regions at the 3' end of the cassette. The R, U5, and U3 regions, the primer binding site and the polypurine tract, and the packaging sequence are compatible with the retroviral components of the packaging cell. Finally, the packaging cell is cultured under conditions that permit the replicase gene cluster to be translated; that permit the replicase to amplify the expression cassette; and that permit the retroviral components to package the expression cassette into retrovirus vector particles.

In one embodiment of the invention, the retrovirus vector includes the replicase gene cluster and the replicase amplification region on the same ribonucleic acid.

In one embodiment, the cell is transduced with an SFV particle comprising the RNA sequences. In another embodiment, the cell is transfected with the RNA sequences.

In another embodiment of the invention, the retrovirus vector is a murine retrovirus vector.

In one embodiment of the invention, the Togavirus is an Alphavirus. In another embodiment, the Togavirus is a Semliki Forest virus.

In another embodiment of the invention, the packaging cell line is selected from the group consisting of PA317, GP+E86, and PHOENIX.

In one embodiment of the invention, the heterologous nucleic acid is a ribozyme or an antisense sequence. In another embodiment, the heterologous nucleic acid carries untranslated genomic regions. In yet another embodiment of the invention, the heterologous nucleic acid is a cDNA. In another embodiment, the heterologous nucleic acid encodes human clotting factor 9.

In one embodiment of the invention, the method further includes separating the retrovirus vector from the packaging cells. In another embodiment of the invention, the method includes the step of infecting a eukaryotic cell with the retrovirus vector.

The invention also provides a nucleic acid sequence with the elements of the retrovirus vector of the method, as described above.

In one embodiment of the invention, the nucleic acid sequence is an RNA.

In another embodiment of the invention, the nucleic acid sequence contains a replicase gene cluster from an Alphavirus, and in yet another embodiment the replicase gene cluster is from a Semliki Forest virus.

In one embodiment of the invention, the nucleic acid sequence includes R, U5, and U3 regions derived from a murine retrovirus.

In another embodiment of the invention, the nucleic acid sequence includes a heterologous nucleic acid the comprises genomic untranslated regions.

In yet another embodiment of the invention, the nucleic acid sequence includes a heterologous nucleic acid that is a cDNA, a ribozyme, or an antisense sequence. In another embodiment, the heterologous nucleic acid sequence encodes human clotting factor 9.

The lower sequence (SEQ ID NO:5) represents the cloning region on the vector pSFV1. The 26S promoter is boxed and the transcription start point of the 26S subgenomic RNA is indicated with an arrow. The nucleotides underlined with asterisks are added to the 5' end of any sequence cloned into the Bam HI site. The upper illustration (SEQ ID NO:4) shows the RPC and the pSFV1-based sequences to the 3' direction, including poly(A) tail, Spe I site inmmediately after it and the Pvu I site used to linearize the SFV-RPC. Change number 1 depicts the location and the sequence of the addition to make the R-regions compatible, while change number 2 indicates the removal of Spe I site and replacing it with Apa I and Swa I.

Figure 3:
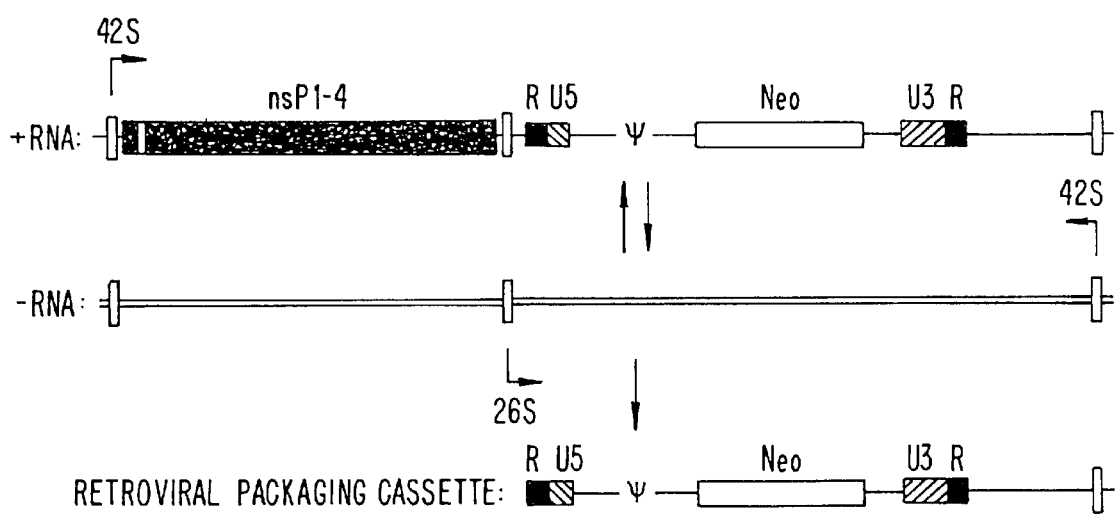

FIG. 3: Structure of Retrovirus Vector Molecules Involved in Cytoplasmic Production of the Retroviral Packaging Cassette The upper structure is positive strand RNA that can act as a messenger RNA for non-structural proteins (nsP1–4, the replicase complex) and serves as a template for minus strand starting at the 42S promoter. The molecule in the middle is the negative strand RNA that serves as a template for the positive strand RNA. Replicase then synthesizes the minus strand subgenomic RNA from the 26S promoter (the lower structure). This molecule represents an equivalent of packageable retrovirus RNA (retroviral packaging cassette, "RPC" or retroviral vector cassette, "RVC"). The lengths of various elements shown are not to scale.

Figure 4:
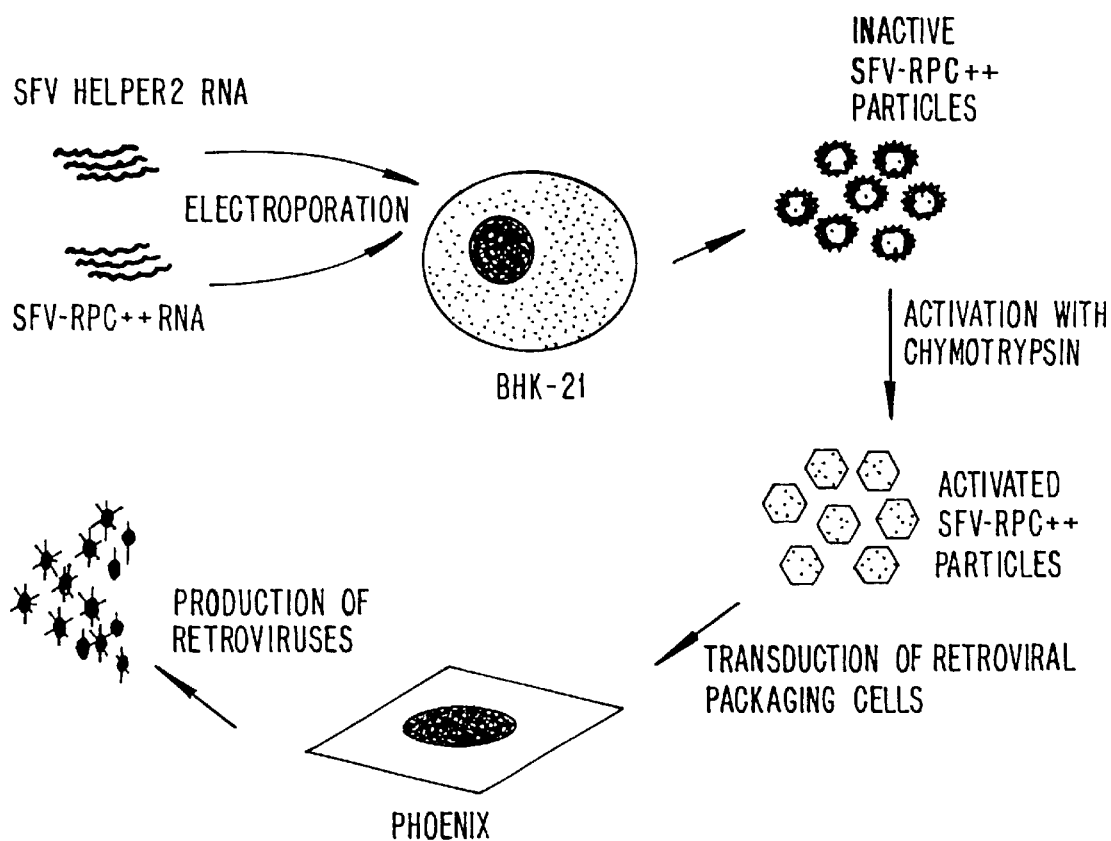

FIG. 4: Schematic Presentation of the System to Package SFV-RPC RNA for Transduction of Retrovirus Packaging Cells and Production of Retrovirus Particles The first phase is to co-electroporate SFV-Helper2 RNA (which provides the genes for synthesis of the SFV structural proteins) and SFV-RPC++ RNA into BHK-21 cells. These cells package the Togavirus-amplified retrovirus vector RNA into SFV particles. The supernatant is harvested and the inactive SFV virions are activated with protease and used to transduce retrovirus packaging cells (PHOENIX). The PHOENIX cells are then amplify and package the retroviral packaging cassette introduced by the SFV particle. The retrovirus containing supernatants are collected sixteen hours later.

DETAILED DESCRIPTION OF THE INVENTION

1. Definitions

Unless defined otherwise, all technical and scientific terms used herein have the meaning commonly understood by one of ordinary skill in the art to which this invention belongs. The following references provide one of skill with a general definition of many of the terms used in this invention: Singleton et al., *Dictionary of Microbiology and Molecular Biology* (2d ed. 1994); *The Cambridge Dictionary of Science and Technology* (Walker ed., 1988); and Hale & Marham, *The Harper Collins Dictionary of Biology* (1991). Although any methods and materials similar or equivalent to those described herein can be used in the practice or testing of the present invention, preferred methods and materials are described. For purposes of the present invention, the following terms are further defined.

A "retrovirus vector" or a "Togavirus-amplified retrovirus vector" is composed of heterologous nucleic acid sequences, usually represented as an expression cassette that includes a transcription unit operably linked to a promoter, flanked by retroviral nucleic acid sequences from the ends of the retroviral genome. The flanking retroviral nucleic acid sequences in the vector allow packaging of the retroviral cassette into virus particles by complementary packaging cells and, following subsequent infection of the packaged retroviral cassette, reverse transcription and integration of the retroviral vector in the transduced host cell. These flanking retroviral sequences usually include the packaging signal ($\psi$), R, U5, U3, and reverse transcriptase recognition sites such as PBS and PPT. The retrovirus vector also contains additional heterologous nucleic acid sequences such as those from Semliki Forest virus, which allows self-amplification and of the retrovirus vector. SFV sequences can also include packaging signals that allow the Togavirus amplified retrovirus vector to be packaged into an SFV particle. Some of these sequences may be present in trans, e.g., the sequences encoding replicase proteins.

A "heterologous nucleic acid sequence" or a "heterologous gene" is a relative term referring to a nucleic acid that is functionally related to another nucleic acid, such as retrovirus vector sequences, in a manner so that the two nucleic acid sequences are not arranged in the same relationship to each other as in nature. The heterologous nucleic acid can originate from a foreign source or from the same source. Modification of the heterologous nucleic acid sequence may occur, e.g., by treating the nucleic acid with a restriction enzyme to generate a nucleic acid fragment that can be operably linked to a promoter or another regulatory element. Modification can also occur by techniques such as site-directed mutagenesis.

An "expression cassette" refers to a series of specified nucleic acid elements that permit transcription of a gene in a target cell. Typically, the expression cassette includes a promoter and a heterologous nucleic acid or gene that is transcribed. Expression cassettes may also include, e.g., transcription termination signals, polyadenylation signals, and enhancer elements.

A "packaging sequence" is a viral nucleic acid sequence that directs efficient and specific encapsidation of RNA into viral particles. Both retroviruses and Togaviruses have a packaging sequences. The retrovirus packaging sequence is also referred to as "$\psi$." An example of a Togavirus packaging signal is nucleotides 1–247 of the SFV genome.

The "R" retroviral nucleic acid sequence is a short direct repeat present at both ends of the retroviral RNA genome. R contains a cap site, and a 3' cleavage and polyadenylation signal for transcription.

The "U5" retroviral nucleic acid sequence is a unique sequence found at the 5' end of the retroviral RNA genome. Together, R and U5, respectively, form the 5' end of the retroviral RNA genome.

The "U3" retroviral nucleic acid sequence is a unique sequence found at the 3' end of the retroviral RNA genome. U3 contains a promoter, including TATA and CCAAT sequences, as well as an upstream transcription enhancer. Together, U3 and R, respectively, form the 3' end of the retroviral RNA genome.

The term "reverse transcriptase recognition sites" refers to retrovirus nucleic acid sequences used by the reverse transcription enzyme to regulate reverse transcription. These sites include nucleic acid regions that are involved in stopping and starting or priming reverse transcription, and may vary according to the specific retrovirus from which they are derived. Such sites include a "primer binding site" (PBS), which is a nucleic acid sequence usually located just downstream of U5 at the 5' end of the retroviral RNA genome. PBS is a sequence complementary to a cellular tRNA that is used to prime reverse transcription. Another such site is a "polypurine tract" (PPT), which is a sequence located just upstream of U3 at the 3' end of the retroviral RNA genome.

After reverse transcription of the provirus, U3, R, and U5, respectively, form the long terminal repeat (LTR), which is a direct repeat found at each end of the DNA provirus.

"Reverse transcriptase" (RT) is a protein encoded by the retroviral gene pol. RT has several activities, including reverse transcription and RNase H activity, that are necessary for transcribing the retroviral RNA genome into provirus DNA. Pol also encodes "integrase," a protein involved in provirus integration into the host genome. RT and integrase proteins are packaged into the infective virion particle along with the retroviral RNA genome.

"Gag proteins" are viral capsid proteins encoded by the retroviral gene gag.

"Envelope proteins" are viral envelope glycoproteins encoded by the retroviral gene env.

"Packaging" cells help replication-deficient vectors, which lack viral protein coding sequences that have been replaced by an expression cassette, to form virus particles that are capable of infecting another host cell. Packaging cells contain mutations so that they cannot supply wild type virus genomes to produce infective particles; their activity is limited to complementing the replication-deficient retrovirus vector and to producing replication-competent virus particles. Packaging cells can either be used to package the retrovirus vector into SFV particles, or to package the RPC into retroviral particles. Examples of packaging cells include, e.g., PA317, PHOENIX, and BHK-21.

"Amphotropic" retroviruses are capable of infecting cells outside of their natural host range, including human cells, as well as cells of their natural host range.

A "promoter" is an array of nucleic acid control sequences that direct transcription of an associated nucleic acid. A promoter includes nucleic acid sequences near the start site of transcription, such as a polymerase binding site. The promoter also optionally includes distal enhancer or repressor elements which can be located as much as several thousand base pairs from the start site of transcription.

A nucleic acid is "operably linked to a promoter" when there is a functional linkage between a nucleic acid expression control sequence (such as a promoter or other transcription regulation sequences) and a second nucleic acid sequence (such as a heterologous nucleic acid), where the expression control sequence directs transcription of the heterologous nucleic acid.

The "replicase gene cluster" is a group of four nonstructural proteins (NSP 1–4) from the Togaviridae viral family that encode the proteins required for replicase enzyme activity. The replicase proteins include the replicative activities required to transcribe minus-strand RNA, which is then used by the replicase proteins as a template to produce new plus-strand genomic RNA or shorter, "26S" RNA that encodes structural proteins.

"Replicase promoter" and "subgenomic promoter" refer to promoters from the Togavinidae viral family. In the wild type virus, a replicase promoter is used by the replicase proteins to transcribe full-length RNA minus strands from the positive strand genome. This full length negative strand in turn serves as a template for two transcripts. The first transcript is a shorter "26S" RNA, which represents about ⅓ of the viral genome and encodes structural proteins. The 26S RNA is transcribed by replicase proteins, using a subgenomic promoter. The second transcript is the positive strand viral genome. The terms replicase and subgenomic promoters refer to promoters recognized by replicase proteins.

A "retroviral packaging cassette" ("RPC") or a "retroviral vector cassette" ("RVC") is a functional term for a nucleic acid region that represents retrovirus sequences and a eukaryotic expression cassette. These sequences are amplified by the replicase activity and packaged as a retroviral cassette by the packaging cell. The retroviral packaging cassette includes an expression cassette that contains, e.g., a heterologous nucleic acid operably linked to a promoter, flanked by retroviral sequences including R, U5, U3, ψ, and RT recognition sites such as PBS and PPT.

The "replicase target sequence" is a functional term for a nucleic acid region, which is composed of the "replicase amplification region" operably linked to a replicase promoter. In a retroviral packaging cell line, the newly translated replicase proteins use a replicase promoter to transcribe the replicase amplification region into minus-strand genomic RNA, and then into plus-strand RNA. The replicase amplification region includes the replicase gene cluster, a replicase promoter, a subgenomic promoter, and the retroviral cassette. The transcription template is plus-strand RNA that has been transduced into the packaging cell, by transfection, infection, or other means of crossing the cell membrane.

A virus or vector "transduces" a cell when it transfers nucleic acid into the cell. Transduction can occur by any means that allows the nucleic acid to enter the cell, e.g., infection, transformation, transfection, or other means of transport across the cell membrane.

A "ribosomal binding site" is a nucleic acid sequence that is involved in ribosome positioning on an RNA for translation.

A "ribozyme" is a catalytic RNA molecule that cleaves a target RNA through ribonuclease activity. The term also encompasses a DNA sequence in an expression cassette from which the RNA is transcribed.

An "antisense" nucleic acid is a nucleic acid that is complementary to another RNA and specifically inhibits expression, e.g., translation or transcription of the complementary RNA or DNA.

An "untranslated genomic region" is a nucleic acid region that is transcribed but does not provide protein coding information for translation, such as an intron or a 3' or 5' untranslated region of an RNA.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof.

"Semliki Forest" virus (SFV) is a species and "Alphavirus" is one of two genera of the viral family Togaviridae (see, e.g., Schlesinger & Schlesinger, Togaviridae: The Viruses and Their Replication, in *Fields Virology*, pp. 825–841 (Fields et al., eds., 3d ed. 1996).

2. Elements of a Togavirus-amplified Retrovirus Vector a. Introduction

The present invention describes Togavirus-amplified retrovirus vectors and a method of making the vectors using a Togaviridae RNA replication system. The retrovirus vectors contain a heterologous nucleic acid in a retroviral cassette, which is packaged into infectious retroviral particles in the packaging cell cytoplasm. The packaged retroviral cassette can be used to infect any cell suitable for expression of a heterologous gene. The Togavirus-amplified retrovirus vector contains at least three main elements: nucleic acid sequences from the family Todaviridae, retrovirus sequences, and a heterologous gene operably linked to a promoter. These elements are incorporated into a recombinant DNA plasmid, which is used in vitro to transcribe a retrovirus vector. The retrovirus vector is then used to transduce packaging cells, which package the retroviral cassette into infectious retrovirus particles. The elements of the retrovirus vector are described below, together with a description of how to make such an retrovirus vector.

b. The Toiavirus Replicase System

Togaviridae is a family of viruses whose genome consists of a single positive strand of RNA. A unique feature of these viruses is that they are replicated in the cell cytoplasm as RNA, without using DNA intermediate. The virus encodes four proteins, nonstructural proteins 1–4 (NSP 1–4), that are required for RNA "replicase" activity. The Togaviridae genomic RNA serves a dual role. It is the messenger RNA for translation of viral replicase activity. The genomic plus-strand RNA also serves as a template for synthesis of a minus-strand RNA by the replicase proteins, which recognize a specific "replicase promoter." The minus-strand is then used by the replicase to amplify a genomic plus-strand RNA and a smaller RNA that encodes structural proteins. The smaller RNA is amplified using a "subgenomic" replicase promoter. (Schlesinger & Schlesinger, Togaviridae: The Viruses and Their Replication, in *Fields Virology*, pp. 825–841 (Fields et al., eds., 3d ed. 1996).

The present invention takes advantage of this extranuclear amplification system to produce Togavirus-amplified retrovirus vectors. The retrovirus vector minimally includes the following sequences from the Togaviridae family: the genes encoding NSP 1–4, the replicase promoter, and the subgenomic promoter. In one embodiment of the vector, the sequences are taken from the Alphavirus genus, and in another specific embodiment the sequences are from the Semliki Forest virus species of Togaviridae, as described in Examples 1–3.

The Togaviridae elements are used in the retrovirus vector in the following manner (see also Liljestrom & Garoff, *Biotechnology* 9: 1356–1361 (1991); Ausubel, supra, p. 16.20.1). The Togavirus-amplified retrovirus vector (RNA) is introduced into retrovirus packaging cells. The replicase proteins (NSP 1–4) are translated from the retrovirus vector (RNA) in the cell cytoplasm. The replicase then transcribes the minus-strand RNA of the retrovirus vector via a replicase promoter. Using the minus-strand, replicase proteins recognize the subgenomic promoter, transcribe, and amplify a retroviral packaging cassette RNA. The amplified retroviral cassette is then packaged by the packaging cells into retrovirus particles. A larger genomic plus-strand RNA is also transcribed via a replicase promoter. However, this RNA is too large to be packaged efficiently. These elements are part of a recombinant DNA plasmid that is used in vitro to transcribe the Togavirus-amplified retrovirus vector RNA, as described below.

c. Retrovirus Sequences

The Togavirus-amplified retrovirus vector contains, in addition to the Togavirus sequences, a retroviral packaging cassette ("RPC") or retroviral vector cassette ("RVC"). This cassette minimally consists of a heterologous gene operably linked to a promoter, flanked by retrovirus sequences, as described below in part d. The retrovirus sequences of the retroviral packaging cassette include at least those sequences necessary for viral packaging, reverse transcription, and proviral integration; that is, the sequences required for a biologically active retrovirus genome that can integrate into a host cell after infection (see, e.g. Fassati et al., Retroviral Vectors, in *Molecular and Cell Biology of Human Gene Therapeutics* pp. 1–19 (Dickson ed., 1995)). In addition, the retrovirus sequences can provide transcription control sequences for a heterologous gene in the retroviral cassette, including sequences such as viral promoters, enhancers, capping signals, and polyadenylation and transcription termination signals. These signals can be further modified by mutation or substitution to provide increased transcription activity.

Any suitable retrovirus can be used as the source for the required sequences, including murine leukemia virus-related "type C" viruses that have been used extensively for gene transfer. Other suitable viruses as a source of sequences include, e.g., monkey, cat, bird, and human retroviruses. One specific embodiment of a virus suitable as a source for retrovirus sequences is the Moloney murine leukemia virus (Mo-MLV), as described in Examples 1–2 (for the nucleotide sequence of Mo-MuLV, see, e.g., Shinnick et al., *Nature* 293: 43–548 (1981)).

Typically, the retroviral packaging cassette will include sequences from the 5' and 3' ends of the viral genome. Both ends of the viral genome contain a short direct repeat called the R region. The viral genome also contains a U5 sequence at the 5' end and a U3 sequence at the 3' end. Thus, the 5' end of the viral genome has the sequences R and U5, while the 3' end of the genome has the sequences U3 and R. These sequences flank the heterologous gene in the retroviral packaging cassette and can be used to regulate its transcription after provirus integration. In addition, the R, U3, and U5 sequences are important for LTR formation and proviral integration.

After reverse transcription and formation of the provirus, R, U3, and U5 form the long terminal repeat (LTR), a direct repeat at each end of the provirus. The LTR contains, respectively, U3, R, and U5. The U3 region contains an enhancer and a promoter, which can be used to drive expression of a heterologous gene in the retroviral packaging cassette, after provirus integration. The R region includes a cap site that is primarily active in the 5' LTR, and a polyadenylation signal that is active in the 3' LTR. These sequences can also be used for capping and polyadenylation of a heterologous gene after provirus integration. One embodiment of R, U3, and U5 sequences from MoMLV, derived from plasmid pLN is described in Examples 1–2 (for a description of the Mo-MuLV insert of pLN, see Miller & Rosman, *BioTechniques* 7: 980–990 (1989)).

A retroviral packaging signal (ψ), which is located downstream of U5, allows packaging of the retroviral cassette into infectious viral particles. The primer binding site (PBS) is at the 3' boundary of the 5' LTR, and is used to prime reverse transcription. PBS and ψ are also typically included in the retroviral cassette. A polypurine tract (PPT) is typically located just upstream of U3 at the 3' end of the RNA genome. Both PPT and PBS are recognized by reverse transcriptase and are involved in regulation of reverse transcriptase activity. Other useful retrovirus sequences can be included in the retroviral packaging cassette, by methods known to those skilled in the art. For example, human retroviruses such as HIV contain other accessory proteins and regulatory nucleic acid sequences that can be included in a Togavirus-amplified retrovirus vector, for example, to target specific cell types. Examples 1–2 describe a specific embodiment of a retroviral cassette derived from the plasmid pLN (Miller & Roseman, supra).

d. Heterologous Gene Sequences and Promoter

The Togavirus-amplified retrovirus vector contains a retroviral packaging cassette (or retroviral vector cassette), which is amplified and packaged as an RNA viral genome into infectious virus particles by packaging cells after introduction of the retrovirus vector to the cells. In the present invention, this cassette includes a heterologous gene or nucleic acid sequence. The heterologous gene can be transcribed in host cells after infection with the packaged retroviral cassette and integration of the provirus into the host cell genome (see Fassati et al., supra). Transcription of the heterologous gene can be regulated by retroviral sequences in the LTR of the provirus, or by a heterologous eukaryotic promoter.

Any heterologous nucleic acid that is suitable for introduction into a host cell can be used in the present invention by one skilled in the art. Genes useful for gene therapy can be introduced into mammals using the methods and vectors of this invention. Genes encoding blood proteins, enzymes, hormones, ribozymes, antisense RNA, viral inhibitors, and ion channel proteins are examples of heterologous nucleic acids useful in gene therapy. Genes encoding selectable markers, such as those that confer antibiotic resistance, can be used to detect and isolate cells transformed with the retroviral packaging cassette. Noncoding nucleic acid sequences can also be introduced into cells.

A functional heterologous gene can be used to replace a mutated gene in a mammal using gene therapy. For example, the gene encoding human clotting factor 8 can be used to treat hemophilia A; the gene encoding human clotting factor 9 can be used to treat hemophilia B; the gene encoding β-globin can be used to treat β-thalassemia; and the gene encoding CFTR can be used to treat cystic fibrosis. Another embodiment of a heterologous nucleic acid used in gene therapy is a ribozyme, which can specifically target and cleave another RNA in the host cell. Yet another embodiment is an antisense nucleic acid, which can be used to inhibit translation of a specific RNA in a host cell. Another specific embodiment of the heterologous nucleic acid is noncoding genomic regions (such as introns), or cDNAs.

A specific embodiment of the invention describes insertion of a Neo gene in the retroviral packaging cassette (Examples 1–2). In another specific embodiment, the gene for human clotting factor 9 is inserted into the retroviral packaging cassette (Example 3).

A typical retroviral packaging cassette contains a promoter operably linked to the nucleic acid sequence encoding the protein. The promoter used to direct expression of the heterologous gene or nucleic acid depends on the particular application. The promoter is preferably positioned about the same distance from the heterologous transcription start site as it is from the transcription start site in its natural setting. As is known in the art, however, some variation in this distance can be accommodated without loss of promoter function. Often the promoter used to drive the heterologous gene is a retrovirus promoter from the LTR region. Other promoters include any promoter suitable it for driving the expression of a heterologous gene in a host cell, including those typically used in standard retrovirus vectors, e.g., SV40 and CMV promoters. In one embodiment of the invention, described in Examples 1–2, the heterologous gene is operably linked to a Mo-MLV retroviral promoter from the U3 retrovirus region. In another embodiment, described in Example 3, the heterologous gene is operably linked to a human clotting factor 9 promoter.

Polyadenylation sequences are also commonly added to the retroviral packaging cassette. Termination and polyadenylation signals that are suitable for the present invention include those derived from retrovirus LTR sequences. Other suitable sequences include polyadenylation and termination sequences derived from SV40, or a partial genomic copy of a gene already resident on the expression vector. In one embodiment of the retroviral packaging cassette, a heterologous Neo gene is linked to the R region retrovirus polyadenylation signal (Examples 1–2).

The retroviral packaging cassette optimally includes enhancer elements that can stimulate transcription up to 1,000 fold from linked homologous or heterologous promoters. Many enhancer elements derived from viruses have a broad host range and are active in a variety of tissues. The retroviral U3 region of various retroviruses, including murine and human viruses, contains an enhancer, which is suitable for use with the heterologous nucleic acid of the packaging cassette. Other enhancers include, for example, the SV40 early gene enhancer, which is suitable for many cell types. Additional enhancer combinations that are suitable for the present invention include those derived from polyoma virus, and human or murine cytomegalovirus (see Enhancers and Eukaryotic Expression (1983)). In one specific embodiment of the invention, described in Examples 1–3, a heterologous gene is linked to the retrovirus enhancer from the U3 region of the LTR.

3. Making and Characterizing a Togavirus-amplified Retrovirus Vector a. Construction of a Retrovirus Vector DNA Plasmid In the present invention, a DNA plasmid is constructed that can be used in vitro to transcribe a retrovirus vector RNA for transduction into packaging cells. This DNA plasmid minimally includes nucleic acids that encode the elements described above: replicase enzyme activity; replicase promoters; a retroviral packaging cassette that contains the retrovirus sequences required for packaging and integration in the host cell; and a heterologous gene operably linked to a promoter.

A recombinant DNA plasmid that can be used to transcribe a retrovirus vector RNA is prepared by first isolating the constituent nucleic acids. The nucleic acids are then joined so that a single recombinant nucleic acid molecule is formed, for example, using restriction endonuclease sites at the ends of the molecule. The recombinant molecule is ligated into a DNA plasmid that is suitable for transcription. Methods for preparing a recombinant nucleic acid are know by those skilled in the art (see Sambrook et al., *Molecular Cloning. A Laboratory Manual* (2d ed. 1989); Ausubel et al., *Current Protocols in Molecular Biology* (1995)).

One preferred method for obtaining specific nucleic acids combines the use of synthetic oligonucleotide primers with amplification on a MRNA or DNA template. Methods such as PCR, LCR, RT and the like are used to amplify the desired nucleotide sequence (see also U.S. Pat. Nos. 4,683,195 and 4,683,202). Restriction endonuclease sites can be incorporated into the primers. Amplified genes can be purified from agarose gels and ligated together. Alterations in the natural gene sequence can be introduced by techniques such as in vitro mutagenesis and amplification using primers that have been designed to incorporate appropriate mutations. Another preferred method uses known restriction endonuclease sites to isolate nucleic acid fragments from DNA plasmids.

The DNA sequence for the Togavirus-amplified retrovirus vector is ligated into a DNA plasmid or other nucleic acid molecule that is used to propagate the insert. Additional elements of the DNA plasmid can include, for example, selectable markers and enhancers. Selectable markers include those that confer antibiotic resistance, e.g., tetracycline resistance or ampicillin resistance, or permit detection and/or selection of those cells transformed with the desired DNA sequences.

After isolation of the recombinant DNA plasmid, it is used in vitro to transcribe the Togavirus-amplified retrovirus vector. DNA plasmids suitable for in vitro transcription of the retrovirus vector are also know to those skilled in the art. These plasmids are commercially available and include promoters for RNA polymerases such as SP6, T7, or T3 (see Sambrook, supra; Ausubel, supra). One embodiment of such a DNA plasmid is described in Example 1–2, plasmids pSFV-RPC and pSFV-RPC++. This plasmid was constructed according to the methods of Examples 1 and 2, using a commercially available SFV1 plasmid, which contains Semliki Forest virus sequences. Moloney murine leukemia virus sequences (Mo-MLV), and a Neo gene were inserted into the SFV1 plasmid as described in Examples 1–2. In another embodiment, described in Example 3, plasmid pSFV-RPC++ with human clotting factor 9 was constructed (see also FIG. 1).

b. In Vitro Transcription of the Togavirus-amplified Retrovirus Vector

As described above, the retrovirus vector is transcribed in vitro from a suitable DNA plasmid containing an RNA polymerase promoter. For in vitro transcription of the retrovirus vector, the plasmid is typically linearized using a suitable endonuclease. Enzymes that provide a 5' overhang or a blunt end are preferred for efficient in vitro transcription. In vitro transcription reactions are very efficient and typically yield 30–50 $\mu$g of RNA per reaction.

An example of in vitro transcription of a retrovirus vector, to produce vector RNA, is provided in Examples 4 and 5. The in vitro transcription reaction is performed using, e.g., the SFV1 plasmid, into which a retroviral packaging cassette is inserted. The SFV1 plasmid is commercially available (Gibco BRL) and contains an SP6 RNA polymerase promoter. The plasmid to be transcribed is linearized with restriction endonuclease Pvu I and purified prior to transcription. The newly transcribed vector RNA is typically purified by LiCl precipitation.

c. Transduction and Packaging of a Togavirus-amplified Retrovirus Vector

After in vitro transcription of the retrovirus vector, the vector RNA is introduced into retrovirus packaging cells via, e.g., infection or transfection, where it acts as an RNA viral genome. The packaging cells can either transiently express the packaging components, by co-introduction of the vector nucleic acid with a plasmid or RNA encoding structural genes for the viral particle, or stable packaging cell lines can be produced.

The retrovirus vector (RNA) can be introduced into packaging cells by any suitable method known to one skilled in the art, for example, infection; electroporation, transfection employing calcium chloride, rubidium chloride calcium phosphate, DEAE-dextran, or other substances; microprojectile bombardment; and lipofection; and other methods (see generally Sambrook et al., supra; Ausubel et al., supra). The particular procedure used to introduce the genetic material into the host cell is not particularly critical. Any of the well known procedures for introducing foreign nucleotide sequences into host cells can be used. Example 4 describes one embodiment of the invention in which the retrovirus vector RNA introduced into retroviral packaging cells using electroporation.

In another embodiment, the retrovirus vector is first packaged as an RNA into SFV particles, using an SFV helper RNA. The SFV particles are then used to infect retroviral packaging cells. Inside the retroviral packaging cells, the RPC is amplified and packaged into retrovirus particles (see Example 4 and FIG. 4). In this embodiment, the vector RNA has an SFV viral packaging site and other cis-acting sequences required for replication of the RNA, while the SFV helper RNA encoding the SFV structural proteins lacks a viral packaging site (packaging site: nucleotides 1–247, replication site: nucleotides 11,423–11,441 of the viral genome; see Liljeström & Garoff, *Biotechnology* 9: 1356–1361 (1991)). The RNAs are introduced into the packaging cell, e.g., via transfection, electroporation and the like. Replicase is translated from the vector RNA. The replicase then amplifies the helper RNA encoding the viral structural proteins. The viral structural proteins are then translated. These proteins recognize the SFV viral packaging signal on the vector RNA and package the retrovirus vector RNA into an SFV viral particle. The broad host range of SFV means that many cells can be used to provide SFV packaging cells lines. Suitable SFV packaging cells include, e.g., BHK-21 cells, HeLa cells, and the like.

Two trans-complementing helper plasmids for SFV are called Helper-1 and Helper-2 (see, e.g., Berglund et al., *Biotechnology* 11: 916–920 (1993)). The Helper-1 packaging vector includes the structural proteins for nucleocapsid formation but lacks a packaging site. The Helper-2 packaging vector is a variant of Helper-1 in which the SFV viral p62 glycoprotein is mutated. Wild type p62 is normally cleaved into its active mature "E2" form by a host cell endoprotease. Mutant p62 cannot be cleaved in vivo and must be cleaved in vitro by chymotrypsin to produce infective particles. This mutation provides an additional biosafety measure.

Once the retrovirus vector has been introduced into a retrovirus packaging cell line, replicase proteins are translated and in turn amplify the RNA retroviral packaging cassette of the retrovirus vector. This cassette contains a retrovirus A site so that it can be packaged by retroviral packaging cells.

Retrovirus packaging cells have been developed as a safe and efficient method of producing retroviral particles (see Miller, *Hum. Gene Ther*. 1: 5–14 (1990)). Typically, packaging cells contain a mutated retrovirus that produces in trans the proteins necessary for formation of a viral particle. However, the packaging cells do not themselves produce packageable retrovirus RNA genomes because they contain retrovirus sequences from which the ψ site has been deleted. Thus, replication deficient retrovirus RNA can be introduced into cells for packaging into retrovirus particles.

Many cell types are suitable for the creation of a packaging cell line, for example, HeLa cells and NIH 3T3 cells. The mutated retrovirus sequences used to make the cell line can be present in many forms, for example, the viral genes encoding the viral capsid components may be separated on different plasmids (Markowitz et al., *Virology* 167: 400–406 (1988)). The host scope of the packaging cell line may also be varied. In the preferred embodiment of the present invention, the packaging cell line is amphotropic and can infect human cells. Embodiments of packaging cell lines used in the present invention are described in Example 4 (e.g., BHK-21 cells, PA317 cells, PHOENIX cells) (Miller & Buttimore, *Mol. Cell. Biol*. 6: 2895–2902 (1986)).

Suitable methods known to those skilled in the art are used to harvest the packaged retroviral cassette from the packaging cell lines (see generally Bunnell & Morgan, Retrovirus-Mediated Gene Transfer, in *Viral Genome Methods*, pp. 3–23 (Adolph ed., 1996)). Generally, after introduction of the Togavirus-amplified retrovirus vector, the packaging cells are incubated under standard cell culture conditions to allow packaging of the retroviral cassette and budding of viral particles into the cell supernatant. The cell supernatant is then collected after a suitable amount of time, e.g., after 24 hours. The supernatant is then frozen or used immediately. Example 4 describes a specific embodiment of this method in which the PA317 cells were electroporated with retrovirus vector RNA and incubated for 24 hours prior to collection of the virus-containing cell-supernatant. In Example 4, PHOENIX, and BHK-21 cells were also electroporated with retrovirus RNA vector.

d. Characterization of Retrovirus Particles and Infected Cells Containing a Retroviral Packaging Cassette Retroviral particles can be characterized by any of a number of means well known to those-of skill in the art, to ensure that they carry the retroviral packaging cassette. These methods include the detection of specific RNA or DNA by well known methods such as northern analysis, dot blot analysis, gel electrophoresis, PCR, and RNase protection assays. Example 4 describes the use of a dot blot method, with hybridization of the membrane to a radioactive probe for the heterologous gene of the retroviral packaging cassette. Examples 4 and 5 also describes the use of Southern analysis to determine integration of the provirus.

The biological activity of the retrovirus particles can be tested by infecting any suitable cell type and examining provirus integration, and RNA and protein expression of the heterologous gene in the retroviral packaging cassette. Cells are infected after titering virus-containing cell supernatants according to standard methods (see Bunnell & Morgan, supra).

A suitable time after infection, cells are examined for retrovirus and heterologous gene activity. Protein expression from the heterologous gene is detected and quantified by any of a number of means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. Provirus integration and RNA expression can be detected by well known methods such as Southern analysis, northern analysis, gel electrophoresis, PCR, RNase protection, radiolabeling and scintillation counting, and affinity chromatography.

To monitor the progress of infection, a marker or "reporter" gene is optionally encoded by the retroviral packaging cassette of the invention. The inclusion of detectable markers provides a means of monitoring the infection of target cells. Markers include components of the β-galactosidase gene, the firefly luciferase gene, the green fluorescence protein, and antibiotic resistance genes (see, e.g., Chalfie et al., *Science* 263: 802 (1994)).

In one embodiment of the invention, biological activity of the retrovirus particles was monitored by selecting infected host cells that were resistant to G418. The Neo gene present in the retroviral packaging cassette conferred resistance to G418 upon host cells, as described in Example 4. Cells that demonstrated G418 resistance were further examined for provirus integration into the host genome using Southern blot analysis, as described in Example 4. In another embodiment, Southern hybridization was used to examine provirus integration into the host cell genome, where the provirus contained the human clotting factor 9 minigene (Example 5).

4. Therapeutic and Scientific Use of a Togavirus-amplified Retroviral Vector a. Introduction The retrovirus vectors of the present invention are used to create retroviral cassette-containing virus particles. These vectors allow efficient and stable expression of a heterologous gene in a host cell. These virus particles can therefore be used in cell transformation procedures for mammalian gene therapy, preferably for human gene therapy. Gene therapy provides methods for combating chronic infectious diseases such as HIV infection, as well as non-infectious diseases such as cancer and birth defects (see generally Anderson, *Science* 256: 808–813 (1992); Yu et al., *Gene Ther.* 1: 13–26 (1994)). Gene therapy can be used to transduce cells with either an ex vivo or an in vivo procedure.

In addition to the powerful therapeutic uses of the vectors and methods of the present invention, the invention is useful for research. Untranslated genomic regions of DNA may be important for regulation of gene expression. Retrovirus vectors are typically transcribed in the nucleus, where they undergo RNA processing. However, the vectors of the present invention are transcribed in the cytoplasm. Thus, the vectors of the invention can be used to introduce nucleic acids into the host cell genome that normally would not be compatible with the retrovirus life cycle, for example, introns, polyadenylation signals, and flanking regions. The activity of these regulatory sequences can then be analyzed.

b. Ex Vivo Gene Therapy

Ex vivo methods for inhibiting viral replication in a cell in an organism involve transducing the cell ex vivo with a vector of this invention, and introducing the cell into the organism. The cells can be hematopoietic stem cells isolated from bone marrow or other cells that are in the host range of the packaged retrovirus particles of the invention. T cells are used in some embodiments in ex vivo procedures.

Several techniques are known for isolating T cells (see, e.g., Leavitt et al., *Hum. Gene Ther.* 5: 1115–1120 (1994)). The expression of surface markers facilitates identification and purification of T cells. Methods of identification and isolation of T cells include FACS, incubation in flasks with fixed antibodies which bind the particular cell type and panning with magnetic beads.

Stem cells are isolated from mammals for transduction and differentiation using known methods. Stem cells are isolated from bone marrow cells by panning the bone marrow cells with antibodies which bind unwanted cells, such as $CD4^+$ and $CD8^+$ (T cells), $CD45^+$ (panB cells), GR-1 (granulocytes), and $Ia^d$ (differentiated antigen presenting cell) (see Inaba et al., *J. Exp. Med.* 176: 1693–1702 (1992)).

In humans, hematopoietic stem cells can be obtained from a variety of sources including cord blood, bone marrow, and mobilized peripheral blood. Purification of $CD34^+$ cells can be accomplished by antibody affinity procedures (see Ho et al., *Stem Cells* 13 (suppl. 3): 100–105 (1995); see also Brenner, J. *Hematotherapy* 2: 7–17 (1993)). Cells can also be isolated and cultured from patients. Alternatively, the cells used for ex vivo procedures can be those stored in a cell bank (e.g., a blood bank). The advantage to using stem cells is that they can be differentiated into other cell types in vitro, or can be introduced into a mammal (such as the donor of the cells) where they will engraft in the bone marrow. Methods for differentiating bone marrow cells in vitro into clinically important immune cell types using cytokines such a GM-CSF, $IFN-_{65}$ and $TNF-\alpha$ are known (see, e.g., Inaba et al., *J. Exp. Med.* 176: 1693–1702 (1992)).

In one embodiment, described in Example 6, murine stem cells are used in an ex vivo procedure for cell transduction and isolation of Neo resistant spleen cells. These cells are also transduced with a vector containing human clotting factor 9. Another embodiment of the invention, described in Example 3, provides a retrovirus vector that includes the gene for human clotting factor 9, which is useful for gene therapy treatment of human patients with hemophilia B.

c. Administration of Retrovirus Particles and Transduced Cells

Packaged retroviral cassette (for in vivo gene therapy) and transduced cells (for ex vivo gene therapy) can be administered directly to a patient, preferably a human. Administration is by any of the routes normally used for introducing a molecule or cell into ultimate contact with blood or tissue cells. Packaged retroviral cassettes of the invention are administered in any suitable manner, preferably with pharmaceutically acceptable carriers. Suitable methods of administering such retroviral particles in the context of the present invention to a patient are known to those skilled in the art.

Pharmaceutically acceptable excipients are determined in part by the particular composition being administered, as well as by the particular method used to administer the composition. Accordingly, there is a wide variety of suitable formulations of pharmaceutical compositions of the present invention. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Parenteral administration and intravenous administration are suitable methods of administration.

The dose administered to a patient, in the context of the present invention should be sufficient to effect a beneficial therapeutic response in the patient over time. The dose will be determined by the efficacy of the particular heterologous gene in the retroviral cassette and the condition of the patient, as well as the body weight or surface area of the patient to be treated. The size of the dose also will be determined by the existence, nature, and extent of any adverse side-effects that accompany the administration of a particular retrovirus particle, or transduced cell type in a particular patient.

For administration, retroviral particles and transduced cells of the present invention can be administered at a rate determined by the transduced cell type, and the side-effects of the vector or cell type at various concentrations, as applied to the mass and overall health of the patient. Administration can be accomplished via single or divided doses. For a typical 70 kg patient, a dose equivalent to approximately 0.1 μg to 10 mg are administered. Transduced cells are optionally prepared for reinfusion according to established methods (see, e.g., Abrahamsen et al., *J. Clin. Apheresis* 6:4 8–53 (1991); Carter et al., *J. Clin. Apheresis* 4: 113–117 (1988); and Aebersold et al., *J. Immunol. Methods* 112: 1–7 (1988)).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example 1

Construction of pSFV-RPC

A recombinant DNA plasmid, pSFV-RPC, was constructed using plasmid SFV1, which is commercially available (Gibco BRL), and a retroviral packaging cassette containing a Neo gene. pSFV-RPC was then used to transcribe a retrovirus vector RNA. The salient elements of the recombinant DNA plasmid, from 5' to 3' were:

(1) The 5' SFV genome containing: (a) the genes for nonstructural proteins 1–4 (NSP 1–4) with a ribosomal binding site; and (b) the replicase subgenomic promoter. The genes for the SFV structural proteins were deleted (see description of the SFV1 vector, Gibco BRL catalogue).

(2) The retroviral cassette containing: (a) R, U5, PBS, and the packaging signal (ψ); (b) the Neo gene; and (d) PPT, U3, and R.

(3) The 3' non-coding region of the SFV genome, including the minus strand replicase promoter (see description of SFV1 vector, Gibco BRL catalogue).

The DNA plasmid was constructed by first isolating a Neo gene fragment flanked by retroviral sequences, then cloning this fragment into a DNA plasmid that completed the flanking retroviral sequences, and finally by cloning the completed retroviral cassette into pSFV1, which contained the SFV sequences.

Restriction endonucleases and DNA modifying enzymes were purchased from New England Biolabs or Gibco BRL. Oligonucleotides were synthesized using an automated DNA synthesizer. Bacterial strains DH5α and STBL2 (Gibco BRL) were used for propagation of plasmid DNA. Unless otherwise stated, bacterial media preparation, restriction endonuclease digests, ligation, and phosphatase treatment of DNA were performed according to standard protocols (Sambrook et al., *Molecular Cloning. A Laboratory Manual* (1989); Ausubel et al., *Current Protocols in Molecular Biology* (1995)).

Figure 1:
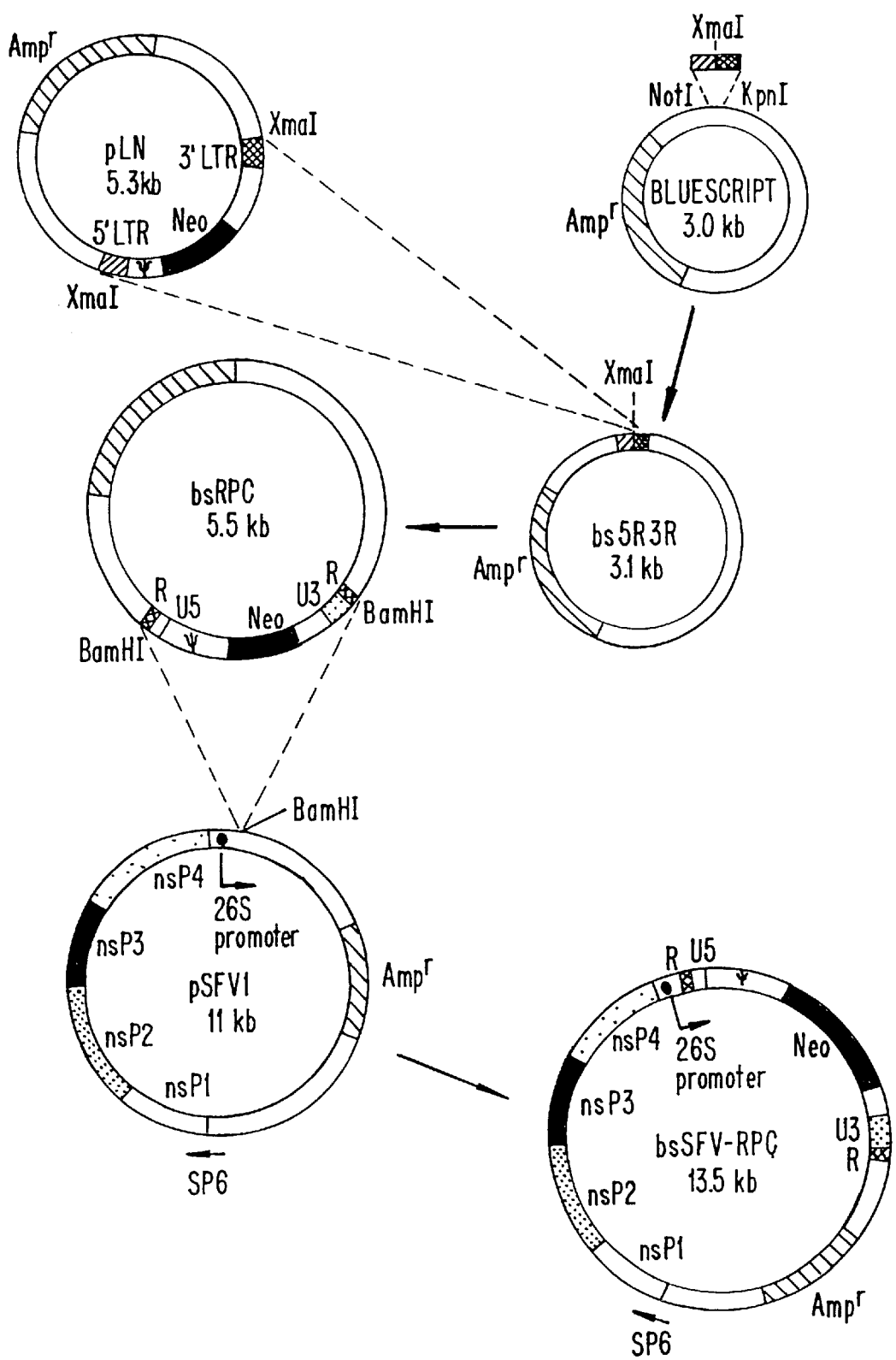
FIG. 1: Schematic Representation of the Construction of the Togavirus-amplified Retrovirus Vector The relevant restriction enzyme sites for each cloning step are indicated, as well as locations of genes or genetic elements in each plasmid. LTR: long terminal repeat of retrovirus; R: repeat region of retrovirus LTR; U5 and U3: unique regions of retrovirus LTR; Ψ: retrovirus packaging signal; Neo: neomycin phosphotransferase gene; nsP1–4: SFV non-structural proteins; 26S promoter: SFV subgenomic promoter for production of packageable retrovirus RNA; SP6 promoter: promoter of bacteriophage SP6 for in vitro production of the full-length RNA. Plasmid maps shown are not to scale.

The steps in the cloning protocol for construction of the retroviral packaging cassette producing SFV plasmid pSFV-RPC are shown in FIG. 1. First, the retroviral packaging cassette was isolated from plasmid pLN by digesting pLN with endonuclease Xma I and isolating the 2.4 kb fragment containing partial 5' and 3' retroviral sequences, ψ, and the Neo gene (5' R-U5-ψ-Neo-U3-R 3') (for a description of the Mo-MLV insert of pLN, see Miller & Rosman, *BioTechniques* 7: 980–990 (1989); for the nucleotide sequence of Mo-MuLV, see, e.g., Shinnick et al., *Nature* 293: 43–548 (1981)). The 2.4 kb Xma I fragment was isolated according to standard procedures.

Second, because this 2.4 kb fragment contains only partial R-regions at both ends, a helper plasmid bs5R3R was created by inserting a synthetic oligonucleotide linker into Bluescript II SK+ (Stratagene, La Jolla, Calif.). This linker fragment complements for the missing parts of the retroviral R-regions and provides all the necessary cloning sites for further steps. The nucleotide sequence of the linker was (upper strand):

5'GGC CGC GGA TCC GCG CCA GTC TTC CGA TAG ACT GCG TCG CCC GGG TAC CCG TGT ATC CAA TAA ACC CTC TTG CAG TTG CAG GAT CCA AGC T 3' (SEQ ID NO: 1)

The linker has endonuclease restriction sites for directed ligation. Not I and Kpn I sites were used to ligate the linkers to Bluescript II SK+, and the linkers also contained Xma I sites for subsequent ligation to the remaining portion of the retroviral cassette.

The double stranded linker was digested with Not I and Kpn I. The Bluescript II SK+ plasmid was digested with Not I and Kpn I, and ligated the linker according to standard procedures (Sambrook et al., supra; Ausubel et al., supra). The resulting DNA plasmid, bs5R3R, was isolated after transformation and screening of DH5α*E. coli* cells according to standard procedures (Sambrook et al., supra; Ausubel et al., supra).

Third, plasmid bs5R3R was digested with Xma I according to standard procedures. The 2.4 kb Xma I fragment containing the remainder of the retroviral packaging cassette (from pLN) was then ligated to bs5R3R as described above. A clone with correct orientation of retroviral sequences was selected and designated as bsRPC. This plasmid contains the complete retroviral packaging cassette, which consists of the Neo gene and its promoter flanked by retroviral sequences R, U5, PBS, and ψ at the 5' end of the retroviral packaging cassette, and ppt, U3, and R at the 3' end of the retroviral packaging cassette. Plasmid bsRPC was isolated after transformation and screening of DH5α*E. coli* cells according to standard procedures (Sambrook et al., supra; Ausubel et al., supra).

Finally, the complete retroviral packaging cassette was isolated from bsRPC by digestion of bsRPC with Bam HI. The 2.5 kb Bam HI fragment containing the retroviral packaging cassette was purified using agarose gel electrophoresis, as described above, for ligation to pSVF1. pSVF1 is commercially available from the SFV Gene Expression System (Gibco BRL, Gaithersburg, Md.) and was created by deleting the coding region of the 26S structural genes from the full-length Semliki Forest virus genome. Deletion of the structural protein genes allows insertion of heterologous nucleic acid into the vector, but retains the replicase promoter, non-structural proteins (NSP 1–4) and the subgenomic promoter (see description in Gibco-BRL catalogue). The resulting plasmid, pSFV-RPC, contains a retroviral packaging cassette (Bam HI fragment from bsRPC) under control of the SFV subgenomic 26S promoter, as well as all the elements required for cytoplasmic autocatalytic replication of the in vitro synthesized RNA. DNA plasmid pSFV-RPC was purified by double CsCl gradient prior to use for in vitro RNA transcription of retrovirus vector RNA (CsCl, Lofstrand Labs Ltd; purification methods, Ausubel et al., supra, pp. 1.7.6 to 1.7.8). The orientation of each of the inserts was checked after every cloning step by restriction enzyme digestions, and the retroviral packaging cassette in plasmid bsRPC was verified by sequencing.

Example 2

Construction of PSFV-RPC++

Figure 2:
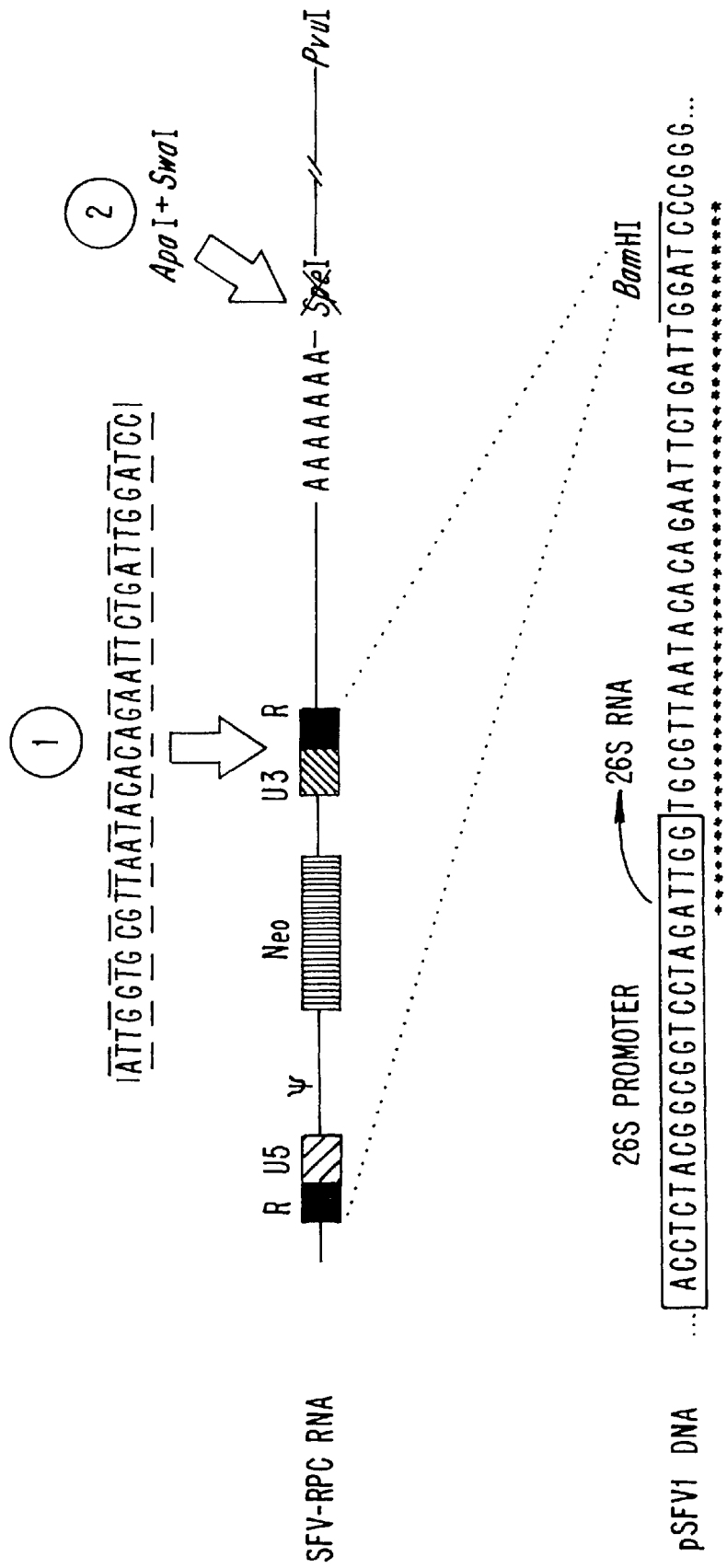
FIG. 2: The Changes Made to SFV-RPC to Create SFV-RPC++

In addition to the vector described in Example 1, a second vector, PSFV-RPC++, was also constructed, according to the procedure described in Example 2, with the following modifications. The original construct pSFV-RPC was redesigned to include certain improvements (see FIG. 2). The first improvement introduced appropriate linearization sites after the poly(A) tail of the SFV vector, because the original Spe I site could not be used with pSFV-RPC (another site is located at the packaging signal region of MoMLV genome). This modification provides a convenient plasmid linearization site for in vitro transcription reactions. A second modification was made to make the 5' and the 3' R-regions fully compatible and allow efficient reverse transcription in a target cell. In the pSFV-RPC expression cassette, a 36 bp 5' addition occurs in the R-region of the resulting RNA due to the structure of the 26S promoter and the cloning site of this vector. Because this stretch of nucleotides cannot be fully removed (the synthesis of 26S RNA is initiated within the 26S promoter sequence, see FIG. 2), a duplicate of this sequence was cloned between the U3 and 3' R regions. After introducing both of the modifications into pSFV-RPC, the resulting construct was named pSFV-RPC++. The detailed cloning strategy is described below and in FIG. 2.

In order to construct the new vector, a 3 kb Spe I fragment of pSFV-RPC, containing most of the packaging signal, Neo gene, U3, the 3' R and all the 3' SFV sequences, was cloned into the Spe I site of the plasmid LITMUS38 (New England Biolabs, Beverly, Mass.). The resulting construct pLRPCSpe was cut with Sac I and Kpn I to remove a 73 bp fragment. This fragment was replaced by a synthetic DNA fragment containing the 36-bp additional SFV sequence resulting in the 5' and the 3' R regions being fully complementary (capital letters in the following sequence represent the addition):

5'gag ctc aat aaa aga gcc cac aac ccc tca ctc ggg ATT GGT GCG TTA ATA CAC AGA ATT CTG ATT GGA TCC gcg cca gtc ctc cga ttg act gag tcg ccc ggg tac c 3' (SEQ ID NO:2) The resulting plasmid pLRPCSpe+ was further modified by replacing the cloning sites from Spe I to Sal I using a synthetic DNA fragment:

5'GGG CCC ATT TAA ATC CTA GG 3' (SEQ ID NO:3)

This modification removed several restriction enzyme sites from the polylinker of pLITMUS38 and provided two sites, Apa I and Swa I, that can be used to linearize the plasmid for in vitro RNA synthesis. This construct, pLRPCSpe++, was cut with Spe I and Avr II, and the 3.1 kb fragment was isolated. To generate pSFV-RPC++,this fragment was ligated to the 10 kb Spe I fragment of pSFV-RPC, a new construct, pSFV-RPC++ was obtained.

Example 3

Construction of a Togavirus-amplified Retrovirus Vector Containing the Human Clotting Factor 9 Minigene A recombinant DNA plasmid, pSFV-RPC++F9prF9, was constructed accroding to Example 2, by inserting human clotting factor 9 minigene operably linked to the human clotting factor 9 gene promoter into pSFV-RPC++. Plasmid pSFV-RPC++F9prF9 was cloned essentially as describedin Example 1 and 2 above, with the following additional steps. The factor 9 minigene insert was excised from the original plasmid (Cornetta et al., Hum. Gene Ther. 7: 1323–1329 (1996)) with Bam HI and cloned into Bcl I site of the plasmid pLRPCSpe++ (see Example 2). Plasmid clone pLRPCSpe++F9prF9/5'3', containing the minigene in correct orientation, was then digested with Spe I and Avr II, and a 5.9 kp fragment was isolated. To generate pSFV-RPC++ F9prF9, this fragment was ligated to the 10 kbp Spe I fragment of pSFV-RPC. The resulting DNA plasmid, pSFV-RPC++F9prF9, was used for in vitro transcription of an SFV-human clotting factor 9 retrovirus vector RNA, as described below in Example 5. In this plasmid, the factor 9 minigene was inserted into pSFV-RPC++ just before the Neo gene at the Bcl I site.

Example 4

Transcription, Packaging. and Infection of PSFV-RPC and RPC++

The following example demonstrates that biologically active retrovirus particles can be produced in the cytoplasm of a packaging cell, using pSFV-RPC and pSFV-RPC++. These retrovirus particles containing the RPC can then be used to infect host cells and integrate as a provirus in the host cell genome.

a. Methods

1. RNA Synthesis In Vitro

Retrovirus vector RNA was transcribed in vitro from pSFV-RPC and pSFV-RPC++ for introduction into packaging cells and production of infectious retroviral particles. The reaction was performed with SP6 MESSAGE mACHINE kit (Ambion Inc., Austin, Tex.). Reactions were performed with additional GTP (1 $\mu$/reaction) in 20 $\mu$l volume at 37° C. for 2 hours. The linearized control plasmid pTRI-Xef from the kit was used as control template. The pSFV3-lacZ or pSFV-Helper2 plasmids from the SFV Gene Expression System kit were linearized with Spe I, extracted with phenol, ethanol precipitated and dissolved in TE buffer to yield a concentration of 1 $\mu$g/$\mu$l. The plasmid pSFV-RPC was linearized with Pvu I and pSFV-RPC++ with Apa I or Swa 1, and 1.5 $\mu$g of linear template was used for RNA synthesis. The samples were treated with DNase I for 15 min at 37° C. and LiCl precipitated according to manufacturers instructions. The resulting retrovirus vector RNA was washed twice with 70% ethanol, air dried and dissolved in 50 $\mu$l of RNAse-free TE buffer. The quality of RNA was monitored by running 2 microliters of each RNA synthesis reaction on 1% agarose, 2.2 M formaldehyde gel in 1×MOPS buffer, followed by staining in running buffer with ethidium bromide. One reaction typically yielded 30–50 $\mu$g of retrovirus vector RNA.

2. RNA Transfection

Retrovirus vector RNA was transfected into retrovirus packaging cells for self-amplification of the RPC and production of infectious retrovirus particles. The retrovirus vector RNA was transfected into the cells by lipofection or electroporation. The liposome-mediated transfection was carried out with Lipofectin (Gibco BRL) using PA317 cells (Miller & Buttimore, *Mol. Cell. Biol.* 6: 2895–2902 (1986)). The PA317 packaging cell line contains amphotropic murine leukemia virus mutated so that it does not produce packageable retrovirus RNA.

The cells were transfected in 6-well plates as follows: $1\times10^5$ PA317 cells were split into each well and incubated 24 hours. For one transfection, 8 μl of Lipofectin and 5 μg of RNA were incubated in 1 ml of OptiMEM (Gibco BRL) at room temperature for 10 min and pipetted onto cells. The plates were incubated with liposome-RNA complex for 3–5 hours and 2 ml of fresh DMEM with 10% serum was added. The plates were incubated overnight and the supernatants were collected 24 hours after transfection, analyzed immediately or stored at −80° C.

For electroporation, logarithmically growing PA317, BHK-21, and PHOENIX cells were trypsinized, washed once with DMEM without serum or phenol red and $1.2 \times 10^6$ cells in 550 μl of the same medium were pipetted into 0.4 cm Gene Pulser cuvette (Bio-Rad, Hercules, Calif.). Up to 50 μg of RNA was mixed with cells in-the cuvette and electroporation was performed immediately with Electro Cell Manipulator ECM 600 (BTX Inc., San Diego, Calif.). Electroporation conditions were, 1 (PHOENIX), 2 (BHK-21) or 3 (PA317) pulses with a pulse length of 7 ms using 250 V. Cells were left to recover 10 min before plating. The contents of the cuvettes were transferred to a 6-well plate with 12 ml DMEM containing 10% fetal bovine serum. The cells were incubated using standard conditions (Bunnell & Morgan, Retrovirus-Mediated Gene Transfer, in *Viral Genome Methods*, pp. 15–16 (Adolph ed., (1996)).

Transfection efficiency was monitored by electroporation of SFV-lacZ RNA as a control. After 24 hours, the cells were washed with PBS, fixed with 4% paraformaldehyde and stained with X-gal solution overnight. The percentage of blue cells resulting from electroporation is the transfection efficiency.

3. SFV and Retroviral Virion Production and Characterization

The electroporated cells of step 2 were incubated according to standard conditions to allow either (1) packaging of the retroviral cassette into retroviral particles; or (2) to allow packaging of the Togavirus-amplified retrovirus vector into SFV particles. Cell supernatant was collected 24 hours after electroporation and frozen at −80° C. or used inmnediately.

For packaging the Togavirus-amplified retrovirus vector into SFV particles, twenty μg of Helper2 RNA along with 40–50 μg of SFV-lacZ or SFV-RPC++ RNA were co-electroporated into BHK-21 cells as described above. The cells were plated on 6-well plates, incubated at 37° C. for 24 hours. Collected supernatants were titered immediately or stored at −80° C. SFV virions made with Helper2 structural proteins were activated before use (Berglund, et al., *Biotechnology* 11: 916–920 (1993)). This was carried out by adding ¹⁄₁₆ volume of chymotrypsin (10 mg/ml, ¹⁄₅₀ volume of $CaCl_2$ (50 mill) and incubating for 15 min at room temperature. The proteinase. was inactivated by adding ¼ volume of Aprotinin-protease inhibitor (500 μg/ml, Sigma) and the activated virus was stored on ice before adding onto cells.

The titer of SFV-lacZ supernatant was determined by plating a serial dilution of the activated virus supernatant on $1-2 \times 10^5$ BHK-21 or PHOENIX cells that were washed once with PBS containing $Mg^{2+}$ and $Ca^{2+}$. The cells were incubated with the virus for 90 min at 37' C. and then incubated in fresh medium for 24 hours. The cells were stained for β-galactosidase activity and titers were determined by counting the blue cells. This biologically determined titer was then used to obtain titer for SFV-RPC++ virions, using essentially the method described for titering retroviruses using a comparative dot blot assay (Onodera, et al., *Hum. Gene Ther.* 8: 1189–1194 (1997)). The dot-blot system binds retroviral RNA to a membrane, which is then probed with a radioactive probe for Neo (see also Ausubel, supra). A manifold dot blot apparatus (Stratagene) was used for the assay.

For the dot blot. assay, serial dilutions of SFV supernatants (180 μL) were applied to a Nytran membrane according to standard conditions, followed by UV-crosslinking. A 2.6 kb Sac II fragrnent from pSFV1, covering most of nsP2 and nsP3 genes, was radioactively labelled and used as a probe. The hybridization and washing conditions were as described for Southern blotting. Autoradiography was carried out with phosphoimager (Fuji BAS-1000) and the signal intensities from the SFV-RPC++ supernatants were compared to those from the titered SFV-lacZ supernatant.

For retrovirus production, logarithmically growing PHOENIX amphotropic or ecotropic cells were transduced with activated SFV-RPC++ SFV viral supernatants (MOI ranging from 0.2 to 100) as described above. Alternatively, the cells were electroporated with SFV-RPC or SFV-RPC++ RNA, as described above. The cells were washed twice with PBS and incubated in their normal growth medium at 32° C. for 16 hours. The supernatants were collected and titered immediately as described below, or frozen and stored at −80° C.

4. Cell Culture and Determination of Retrovirus Titers

The biological activity (i.e., viral transduction of target cells, reverse transcription of the RNA genome, proviral integration into the genome of the target cell, and the expression of the Neo transgene) of the packaged retrovirus was evaluated by titering virus-containing cell supernatants on mouse and human cells (NIH 3T3 and HeLa or TE671 cells respectively, obtained from ATCC) according to standard methods (Bunnell & Morgan, supra).

All retrovirus packaging cells were grown in Dulbecco's Modified Eagle Medium with high glucose (4.5 g/1) and 10% fetal bovine serum. The BHK-21 (ATCC CCL-10) were grown in G-MEM complete medium (G-MEM, 2 mM glutamine, 20 mM HEPES, 10% tryptose phosphate broth, 5% FBS). The retrqvirus packaging cell lines used in this study were the murine NIH3T3-based amphotropic cell line PA317 (Miller et al., *Mol. Cell. Biol.* 6: 2895–2902 (1986)), the human HT1080 based cell line FLY with either amphotropic (A13) or cat endogenous virus (RD18) envelope (Cosset et al., *J. Virol.* 69: 7430–7436 (1995) or the human 293-T based cell line PHOENIX (Dr. Gary Nolan, Stanford University, Stanford, Calif., available from the ATCC) with either ecotropic or amphotropic envelope containing cell lines. The murine fibroblast cell line NIH3T3 (ATCC CRL 1658), human cervical carcinoma cell line HeLa (ATCC CRL 7923) or human rhabdyosarcoma cell line TE671 (ATCC CRL 8805) were used for vector titer determination. A population of control GlNa vector-transduced human Sup T1 T-cells were used a standard (Ragheb et al., *AIDS Res. Hum. Retrovir.* 11: 1343–1353 (1995).

The transduced cells were selected for their resistance to 0.8 mg/ml G418 antibiotic (Bunnell & Morgan, supra) and colonies from serial dilutions were counted. Biological titers on human or mouse cells varied from 5 to 30 G418 resistant cfu/ml. Colonies from different electroporations were isolated, expanded in culture, and stored at −80° C.

To determine the ability of cell supernatants to transfer resistance to the antibiotic analog G418 (Gibco-BRL), both mouse (NIH3T3) and human (HeLa or TE671)) cells were plated at a density of $1 \times 10^5$ cells per well of a 6-well plate. Twenty four hours after plating the supernatants from transfected retrovirus packaging cells were filtered through 0.45 μm and diluted serially into medium containing 8 μg/ml Polybrene. The monolayers of NIH3T3 or HeLa cells were covered with 2 ml of diluted viruses and the transduction was carried out either by incubating 24 hours at 37° C. or first spinning the cells at 32° C., 3000 rpm for 1 hour and then incubating at 32° C. for 23 hours. Transduced cells were selected for their resistance to 0.8 mg/ml G418 and surviving colonies were stained with methylene blue—methanol.

5. Southern Blot Analysis of Provirus Structure

Integration of provirus in the genome of G418 resistant cells was shown by Southern blot. Chromosomal DNA was prepared from G418 resistant colonies. Southern blot analysis was performed according to standard methods (Southern, *J. Mol. Biol.* 98: 503–517 (1975); Ausubel et al., supra). Radioactive probes that hybridized to the Neo gene were used to verify that the integrated proviruses were intact.

To perform the Southern blot analysis, the G418 resistant NIH3T3 or HeLa cell populations from titering were expanded and cellular DNA was isolated with Nucleon II kit (Scotlab, Inc., Strathclyde, Scotland, UK). Ten μg of DNA was digested with restriction enzymes overnight according to manufacturers recommendations. After electrophoresis in 1% agarose gel, followed by denaturing and neutralization of the gel, the DNA was transferred to Nytran nylon membrane (Schleicher & Schuell, Keene, N.H.) and the membrane was UV-crosslinked in Stratalinker (Stratagene), followed by prehybridization at 42° C. in solution containing 35% dextran sulfate, 7×SSPE, 0.7% SDS, 20% formamide, 5×Denhardt's solution and 200 μg of denatured salmon sperm DNA. A $^{32}$P-labeled 500 bp Eco RI—Nco I fragment from pLN, containing the most of the Neo gene coding sequences, was denatured and used as a probe in the prehybridization solution overnight at 42° C.

Autoradiography was carried out to the washed filter with X-ray film visualization or with phosphoimager analysis (Fuji BAS-1000) for quantitation. In addition to the Neo probe, a probe was used to characterize the 5' end of the proviral DNA. This Spe I—Bsr GI-fragment from pLN contains the MoMLV packaging signal and recognizes sequences upstream from the Neo gene. GlNa vector-transduced Sup T1 cells were used as a control cell line (Ragheb, et al., *AIDS Res. Hum. Retrovir.* 11: 1343–1353 (1995).

b. Results

1. In Vitro Synthesis of Retrovirus Vector RNA

The general organization of the SFV-RPC molecule is shown in FIG. 3. When the plasmid clone containing SFV self-amplifying unit (promoters at the both ends for nsPl-4 enzyme complex and the gene cluster encoding nsP1–4), 26S promoter and the RPC++, is linearized with Apa I and transcribed in vitro with SP6 RNA polymerase, an RNA species of approximately 11 kb is produced. Upon transfection into retrovirus packaging cells, this RNA is first translated to produce replicase enzyme complex, nsP1–4. The replicase then starts to synthesize the full-length minus strand RNA, that has a dual role: it works as a template for synthesis of more plus strand RNA and also serves as a template for subgenomic plus strand RNA production, starting from the 26S promoter. This RNA resembles the retrovirus virion RNA and could potentially be packaged into virus particles provided in trans by the host packaging cell.

The synthesis of the transfectable RNA was carried out with SP6 RNA polymerase, using a method that produces 5' capped RNA. SP6 polymerase starts the synthesis of the complementary RNA from the specific promoter sequence that is included in the plasmid pSFV1. The control plasmid pSFV-lacZ was linearized at Spe I site, creating a template of 11.3 kb and also providing a short poly(A) tail to the final subgenomic RNA. Because this particular site cannot be used in the case of pSFV-RPC, a Pvu I in the backbone of the plasmid was used. The use of this site yields extra 1.4 kb to the final product, thus creating an RNA species of 12.1 kb.

When pSFV-RPC++ was linearized with Apa I or Swa I and used as a template in in vitro transcription reaction, high molecular weight RNA species were synthesized.

2. RNA Transfer into Retrovirus Packaging Cell Lines

Using the in vitro synthesized SFV-LacZ RNA, RNA gene transfer into retrovirus packaging cell lines was tested. Electroporation has been previously reported to be an effective RNA transfection method to introduce SFV RNA's into BHK cells (Liljestrom et al., *BiolTechnology* 9, 1356–1361 (1991)). In addition to electroporation, calcium phosphate coprecipitation and lipofection were tested as methods to mediate SFV-LacZ RNA transfers into the PA317 retroviral packaging cell line. No appreciable amount of LacZ-positive staining cells were observed 24 hrs post calcium phosphate-mediated SFV-LacZ RNA transfection into PA317 cells. In contrast, lipofection of SFV-LacZ RNA was successful with optimal conditions for liposome-mediated RNA transfection appearing to be 8 μl of Lipofectin reagent and 5 μg of RNA for 2×10$^5$ cells in 1 ml volume of OptiMEM. It should be noted that control DNA lipofections into PA317 cells with 10 μg of a plasmid containing lacZ gene transcribed by the CMV promoter always resulted in higher than 10% transfection efficiencies.

The amphotropic PA317 cell line was used to determine the optimal conditions for SFV RNA electroporation. Initial experiments using 10 μg of SFV-lacZ RNA with different number of pulses and various voltages with 7 ms pulse length revealed the optimal conditions described in the methods section. Also, increasing the amount of RNA per reaction up to 50 μg increased the number of transduced cells, indicating a correlation between the RNA amount and SFV RNA transfer efficiency. Maximal electroporation efficiency appeared to be routinely 5–10% under optimal conditions and the best efficiency ever obtained with this technique was about 15%.

Several other types of retrovirus packaging cell lines were next tested for their efficiency of electroporation with SFV RNA. Four human cell-based lines were tested; FLY A13 or FLY RD18 cells (based on human fibrosarcoma cell line HT1080) and PHOENIX amphotropic and ecotropic cells (based on human embryonic kidney cell line 293-T). The FLY cells had lower transfection efficiencies with SFV RNA, whereas the efficiency with plasmid DNA was about 50%. In contrast, PHOENIX cells were equally transfectable with plasmid DNA and SFV RNA, yielding routinely 50–70% efficiency, and were chosen for further studies.

3. Production of SFV-mediated Retroviral Packaging Cassetes using RNA Electroporation In the first experiments, the retrovirus packaging cell line PA317 was transfected (using electroporation conditions described above) with pSFV-RPC or pLN DNA as a positive control. Cell culture medium was then analyzed for the presence of biologically active retroviruses by titering on both mouse and human cells. The original SFV-RPC RNA yielded titers lower than 10 G418$^R$ cfu/ml, whereas transient titers using 5–10 μg LN plasmid were routinely higher than 1000 G418$^R$ cfu/ml. When optimized conditions for RNA synthesis and electroporation (see above) were used and the amount of RNA per electroporation was increased, retrovirus titer of 150 G418$^R$ cfUi/ml on TE671 cells could be obtained. In this same experiment, 10 μg of LN plasmid DNA yielded titer of 1250 G418$^R$ cfu/ml.

The retroviral R-regions of the SFV-RPC RNA are not identical. The modifications indicated in FIG. 2 were introduced to RPC to yield a second vector (containing identical R-regions), designated pSFV-RPC++. In the second set of experiments, this RNA, along with the SFV-RPC RNA and LN DNA, were electroporated into PA317 and PHOENIX amphotropic or ecotropic packaging cells. After 24 hours, the resulting supernatants were titered on both NIH3T3 and TE671 cells (Table 1). The experiment was repeated with 30 μg of each nucleic acid and obtained again a linear correlation between the amount of RNA in electroporation and the titer obtained. These data also demonstrate the higher efficiency of PHOENIX cells compared to PA317 cells, yielding 1.5–2 times higher titers, especially when more RNA was used. Taken together, with the modifications made to the RPC, the retrovirus vector titers were raised to $4 \times 10^3$ G418$^R$ cfu/ml (using PHOENIX ecotropic cells).

TABLE 1

Vector Production Using Electroporation.

| Sample[a] | Titer on NIH/3T3[b] | Titer on TE671[b] |
|---|---|---|
| 10 μg | | |
| LN DNA/PA317 | 250 | 550 |
| LN DNA/Phoenix A | 150 | 150 |
| LN DNA/Phoenix E | 135 | n.d. |
| RVC RNA/PA317 | <5 | 10 |
| RVC RNA/Phoenix A | 5 | <5 |
| RVC RNA/Phoenix E | 10 | n.d. |
| RVC ++ RNA/PA317 | 500 | 950 |
| RVC ++ RNA/Phoenix A | 400 | 550 |
| RVC ++ RNA/Phoenix E | 500 | n.d. |
| 30 μg | | |
| LN DNA/PA317 | 1000 | 1500 |
| LN DNA/Phoenix A | 1800 | 3000 |
| LN DNA/Phoenix E | 1750 | n.d. |
| RVC RNA/PA317 | 35 | 5 |
| RVC RNA/Phoenix A | 60 | 10 |
| RVC RNA//Phoenix E | 35 | n.d. |
| RVC ++ RNA/317 | 2500 | 1700 |
| RCV ++ RNA/Phoenix A | 2000 | 4000 |

[a] = Nucleic acid samples were electroporated into the indicated packaging cell lines, and samples collected 24 hr post-electroporation.
[b] = G418$^R$ cfu/ml
n.d. = not determined 4. Production of SFV-mediated Retroviral Packaging Cassettes using SFV-RPC++ virions As the correlation between the RNA amount and the titers was linear, the use of SFV virions was tested as carriers of RPC++ RNA to retrovirus packaging cells. This system is illustrated in FIG. 4. SFV-lacZ virions were produced and activated as indicated above. These viruses were then used to transduce PA317, PHOENIX, FLY A13 and BHK-21 cells, followed by staining for β-gal activity 24 hours later. The PHOENIX cells appeared to give the best transduction efficiency with SFV (typical yield>90% SFV transduction efficiency).

The initial set of experiments to produce retroviruses in PHOENIX cells using SFV-RPC++ virions were carried out with a low MOI of 0.2. The titer from this preliminary study was $4 \times 10^3$ G418$^R$ cfu/ml, which was the same as the best result with the RNA electroporation system. The next series of experiments were carried out to determine the kinetics of retrovirus production with this system. In this experiment, $3 \times 10^6$ PHOENIX ecotropic and amphotropic cells were transduced with SFV-RPC++ (MOI=0.5), the supernatants were collected every 6 hours and titered on NIH 3T3 cells. Resultant titer data indicate that majority of the SFV-derived retrovirus production occurs during the first 12 hours after transduction. In total, this experiment yielded $3 \times 10^4$ G418$^R$ cfu from ecotropic cell line and $2 \times 10^4$ G418$^R$ cfu from amphotropic cell line during 24 hours of production.

A third transduction was performed with a high MOI of SFV-RPC++ (100) to demonstrate the capacity of this system. In addition, the transduced PHOENIX cells were incubated at 32° C. 16 hours to minimize the retrovirus turnover during the production period. As presented in Table 2, the titers from this experiment range from $5 \times 10^4$ to $1.5 \times 105$ G418$^R$ cfu/ml, depending on the packaging cell type and the cell line used for titering. Taken together, $1.1 \times 10^6$ infectious retrovirus particles were produced during 24 hours (this is $7.5 \times 10^5$ particles 124 hours/$10^6$ cells). When supernatants produced by PHOENIX ecotropic cell line were titered on human cell line TE671, no G418$^R$ colonies were detected. The vector preparations were also free of replication competent retrovirus (RCR).

TABLE 2

Retroviral Particle Production Using SFV Transduction

| SFV-Transduced Packaging Cell Line[a] | Titer on NIH/3T3[b] | Titer on TE671[b] |
|---|---|---|
| Phoenix E | $1.5 \times 10^5$ | <5 |
| Phoenix A | $5 \times 10^4$ | $8 \times 10^4$ |

[a] = SFV-RVC ++ virions were used to transduce the indicated cell line (moi = 100) and cells cultured at 32° C. for 16 hr.
[b] = Medium from transduced cell lines were collected 16 hours post-transduction and the number of G418$^R$ cfu/ml determined.

5. Analysis of Proviral Structure in Cells Transduced with SFV-based Retroviruses Several populations of G418-resistant colonies of NIH3T3 and HeLa cells, obtained from titering experiments of SFV-RPC-based PA317 supernatants, were subjected to Southern blot analysis in order to determine the genomic structure of proviral DNA. These populations were derived from the last well of the titration dilution series and were composed of a small number of individual colonies (<5) of varying size (some 2–3 time larger than others). Two possible structures could confer G418 resistance; only one is the bona fide provirus structure (the other structure is the RPC itself). Upon Southern blotting and probing with either Neo or ψ probe, both of the possible provirus structures would yield the same size Sma ψ fragment (2.4 kb), but only the correctly reversed transcribed provirus would yield the Xba I fragment of 2.4 kb. Also, Eco RI, either alone or in concert with Xba I was used to determine the more precise nature of the proviruses.

Probing with radioactive Neo-fragment revealed Sma I, Xba I and Xba I+Eco RI bands expected for the predicted proviral DNA structure. The different sizes of the Eco RI fragments in each cell population indicates variable distance to the nearest Eco RI site in the flanking DNA downstream from the 3' LTR. The results in a second experiment were identical to the results from NIH3T3 cells and indicate a correct provirus structure, created by reverse transcription.

The Southern blots demonstrated that all of the isolated G418 resistant colonies had the predicted 2.4 kb Sma I fragment that hybridized to the Neo probe. This results indicates that the integrated Neo gene is flanked by retrovirus R regions. In addition, digestion with Xba I yielded the same 2.4 kb fragment, indicating that the integrated provirus was correctly reverse transcribed and flanked by perfect retroviral LTRs. Thus, these molecular analysis demonstrate that SFV-promoted RPC RNA can be packaged, appropriately reverse transcribed, and integrated into the genome of target cells in an identical manner to standard retrovirus vectors.

Example 5

Transcription. Packaging, and Infection of pSFV-RPC and RPC++ Containing the Human Clotting Factor 9 Minigene The procedures of Example 4 were repeated, substituting the vector containing human clotting factor 9 minigene for the vectors containing the Neo gene. Southern analysis indicated that the provirus containing the human clotting factor 9 minigene was correctly integrated into the host cell genome.

Retrovirus vector RNA was transcribed using pSFV-RPC++F9prF9, SFV-RPC++F9prF9 virions were produced and PHOENIX amphotropic retroviral packaging cells were transduced essentially as described in Example 4. Retrovirus-containing supernatants were collected 16 hours later and used to transduce TE671 cells. The cell population was then selected for the resistance to G418, since RPC++ F9prF9 also contains the Neo gene. The supernatant was then analyzed for human clotting factor 9 production by ELISA, using the commercially availbie Asserachrom IX:Ag kit (Diagnostica Stago, Asnieres, France). ELISA showed that the cells transduced with the retroviruses (packaged in PHOENIX cells transduced with SFV-RPC++ F9prF9 virion particles) are capable to produce significant amount of Factor 9, even several weeks after the transduction.

A PCR system, designed to distinguish between intron-containing and intronless proviruses, was used to verify the structure of the integrated provirus. PCR clearly demonstrates that the 500 bp Factor 9 mini-intron is still present in the integrated viral sequences. This result was also confirmed by Southern blot, using human factor 9 cDNA as a probe.

Example 6

Ex Vivo Gene Therapy in Mice

Murine bone marrow cells can be isolated and infected with the SFV-Neo retrovirus particles containing pSFV-RPC and pSFV-RPC++ containing either the Neo gene or the clotting factor 9 gene, described above in Examples 1–4. The infected cells are reintroduced to the donor mice. After spleen colonies are isolated from recipient mice, the cells are analyzed for the presence of RPC provirus and Neo or clotting factor 9 gene expression.

Murine bone marrow cells are isolated according to standard methods (see, e.g., Miller et al., *J. Virol.*, 62:4337–4345 (1988)). The isolated murine bone marrow cells are infected with retrovirus particles containing the retroviral packaging cassette according to the methods described above. The cells are then injected into the donor mice. Twelve days postinjection, spleen colonies are dissected out and cultured in vitro.

The spleen colonies are examined for Neo gene expression by isolating G418 resistant clones, as described above. Chromosomal DNA is isolated from G418 resistant cells and is examined for provirus integration, as described above. Spleen colonies are examined for clotting factor 9 gene expression by isolating chromosomal DNA from cells and examining the cells using dot blot analysis. Provirus integration is confirmed using Southern blots, as described above.

What is claimed is:

1. A method for packaging a heterologous nucleic acid into a retrovirus vector within a packaging cell, the method comprising the steps of:
   (a) selecting a packaging cell that produces retroviral components including reverse transcriptase, integrase, gag proteins, and envelope proteins;
   (b) transducing the cell with a positive strand RNA comprising, from 5' to 3', the following components:
      (i) genes encoding non-structural proteins 1–4 of the replicase gene cluster of a togavirus, said replicase gene cluster operably linked to a ribosomal binding site recognized by ribosomes of the packaging cell,
      (ii) a complement of a Togavirus 26S subgenomic promoter, (iii) a retroviral packaging cassette, the retroviral packaging cassette comprising, from 5' to 3': R and U5 regions at the 5' end, a primer binding site, a retroviral packaging sequence, a eukaryote expression cassette comprising a promoter operably linked to a heterologous nucleic acid, a polypurine tract, and U3 and R regions at the 3' end of the retroviral packaging cassette; wherein the R, U5, and U3 regions, the primer binding site, the polypurine tract, and the packaging sequence are compatible with the retroviral components of the packaging cell; and, (iv) a Togavirus 42S negative strand genomic promoter operably linked the positive strand RNA; and (c) culturing the cell under conditions that permit the replicase gene cluste to be translated into replicase; that permit the replicase to amplify a negative strand RNA using the 42S promoter operably linked to the positive strand RNA; that permit the replicase to amplify the retroviral expression cassette using the 26S subgenomic promoter operably links to the complement of the retroviral expression cassette on the negative strand RNA, and that permit the retroviral components to package the expression cassette into retrovirus vector particles.

2. The method of claim 1 wherein the cell is transduced with an SFV particle comprising the RNA sequences.

3. The method of claim 1 wherein the cell is transfected with the RNA sequences.

4. The method of claim 1 wherein the retrovirus vector is a murinc retrovirus vector.

5. The method of claim 1 wherein the Togavirus is an Alphavirus.

6. The method of claim 1 wherein the Togavirus is Semliki Forest virus.

7. The method of claim 1 wherein the packaging cell line is selected from the group consisting of PA 317, GP+E86 and PHOENIX.

8. The method of claim 1 wherein the heterologous nucleic acid is a ribozyme or an antisense sequence.

9. The method of claim 1 wherein the heterologous nucleic acid carries untranslated genomic regions.

10. The method of claim 1 wherein the heterologous nucleic acid is a cDNA.

11. The method of claim 1 wherein the heterologous nucleic acid is a nucleic acid sequence encoding human clotting factor 9.

12. The method of claim 1 which further comprises the step of separating the retrovirus vector from the packaging cells.

13. The method of claim 1 which further comprises the step of infecting a eukaryotic cell with the retrovirus vector.

* * * * *